(12) United States Patent
Jansson et al.

(10) Patent No.: US 11,446,420 B2
(45) Date of Patent: Sep. 20, 2022

(54) CONNECTOR ARRANGEMENT, A SYSTEM FOR EXTRACORPOREAL BLOOD TREATMENT AND A METHOD FOR PRIMING A FLUID CHAMBER OF A BLOOD TREATMENT UNIT

(71) Applicant: GAMBRO LUNDIA AB, Lund (SE)

(72) Inventors: Olof Jansson, Vellinge (SE); Michael Pettersson, Malmo (SE)

(73) Assignee: Gambro Lundia AB, Lund (SE)

( * ) Notice: Subject to any disclaimer, the term of this patent is extended or adjusted under 35 U.S.C. 154(b) by 547 days.

(21) Appl. No.: 16/464,594

(22) PCT Filed: Nov. 21, 2017

(86) PCT No.: PCT/EP2017/079850
§ 371 (c)(1),
(2) Date: May 28, 2019

(87) PCT Pub. No.: WO2018/099758
PCT Pub. Date: Jun. 7, 2018

(65) Prior Publication Data
US 2021/0100946 A1    Apr. 8, 2021

(30) Foreign Application Priority Data
Nov. 29, 2016    (SE) .................................. 1651563-7

(51) Int. Cl.
*A61M 1/36*  (2006.01)
*A61M 1/16*  (2006.01)
*A61M 1/00*  (2006.01)

(52) U.S. Cl.
CPC .......... *A61M 1/3649* (2014.02); *A61M 1/165* (2014.02); *A61M 1/365* (2014.02);
(Continued)

(58) Field of Classification Search
CPC .. A61M 1/3649; A61M 1/165; A61M 1/3624; A61M 1/365; A61M 1/3653;
(Continued)

(56) References Cited

U.S. PATENT DOCUMENTS

| 4,681,606 | A | * | 7/1987 | Swan, Jr. | ........... B01D 19/0042 96/197 |
| 5,505,210 | A | * | 4/1996 | Clement | ............. A61M 39/223 600/566 |

(Continued)

FOREIGN PATENT DOCUMENTS

| DE | 8904529 U1 | 5/1989 |
| EP | 0747074 B1 | 12/1996 |

(Continued)

OTHER PUBLICATIONS

International Search Report for International Application No. PCT/EP2017/079850 dated Apr. 23, 2018; (3 pages).

*Primary Examiner* — Krishnan S Menon
(74) *Attorney, Agent, or Firm* — K&L Gates LLP

(57) ABSTRACT

A connector arrangement (10) for connecting to a fluid chamber (6) of a blood treatment unit (4) for extracorporeal blood treatments. The connector arrangement (10) includes a connector device (11) with a connector body (47) comprising a port opening (43) and an interior wall (50) defining a port space (39) designed to receive a first fluid port (8A) of the fluid chamber (6). The connector device (11) also incorporates a fluid path (35*a*) extending from the port space (39) to a first end opening (51) of the connector device (11), and an air path (36*a*) extending from the port space (39) to a second end opening (52) of the connector device (11), wherein the fluid path (35*a*) and the air path (36*a*) are separate paths. Also a system (1) for extracorporeal blood (Continued)

treatment including the connector arrangement (10) and a method for priming the fluid chamber (6).

21 Claims, 4 Drawing Sheets

(52) U.S. Cl.
CPC ........ *A61M 1/3624* (2013.01); *A61M 1/3653* (2013.01); *A61M 1/782* (2021.05); *A61M 1/86* (2021.05)

(58) Field of Classification Search
CPC .................... A61M 1/782; A61M 1/86; A61M 2039/1027; A61M 39/105
See application file for complete search history.

(56) References Cited

U.S. PATENT DOCUMENTS

| | | | | |
|---|---|---|---|---|
| 5,520,640 | A * | 5/1996 | Utterberg | A61M 1/3627 604/80 |
| 5,769,815 | A * | 6/1998 | Utterberg | A61M 1/3627 210/239 |
| 5,858,239 | A * | 1/1999 | Kenley | A61M 1/3627 210/646 |
| 5,951,870 | A * | 9/1999 | Utterberg | A61M 1/3647 210/645 |
| 6,192,900 | B1 * | 2/2001 | Amal | A61M 1/168 134/22.1 |
| 8,875,748 | B2 | 11/2014 | Beden et al. | |
| 2008/0097274 | A1 * | 4/2008 | Neri | A61M 1/3627 604/6.15 |
| 2009/0320684 | A1 | 12/2009 | Weaver et al. | |

FOREIGN PATENT DOCUMENTS

| | | |
|---|---|---|
| EP | 2599518 A1 | 6/2013 |
| EP | 3144022 A1 | 3/2014 |
| WO | 2015/174420 A1 | 11/2015 |

\* cited by examiner

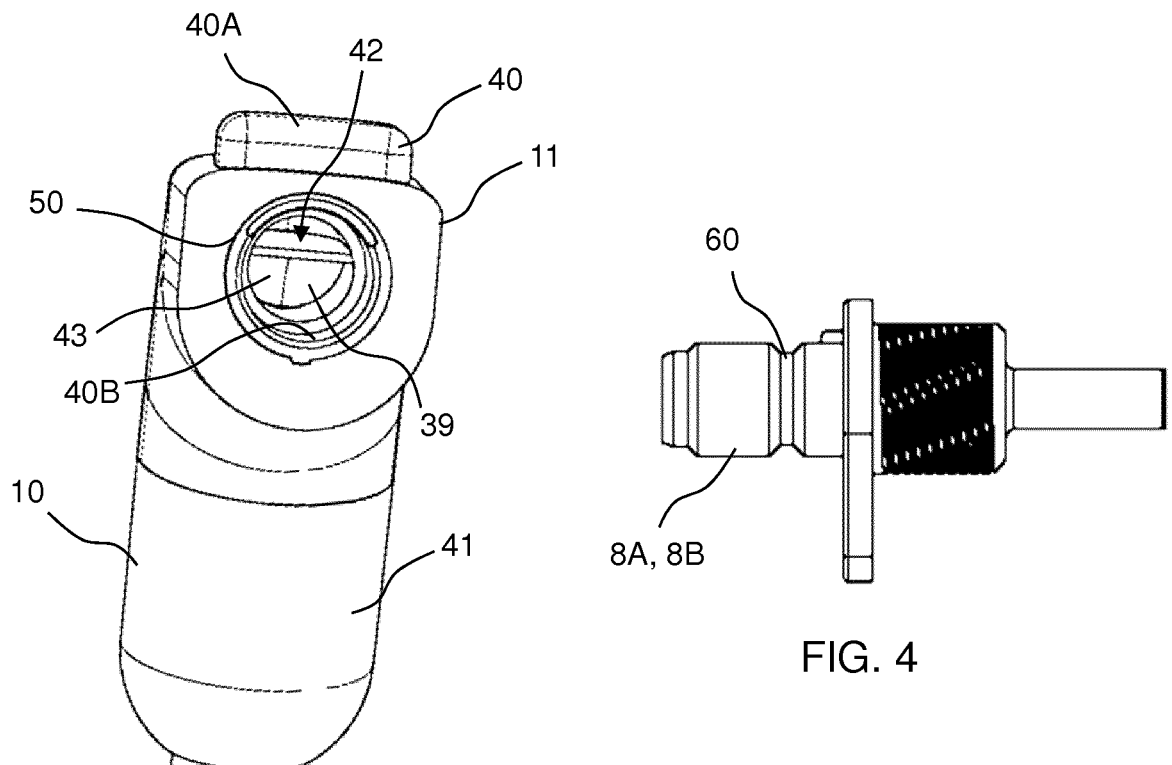
FIG. 4
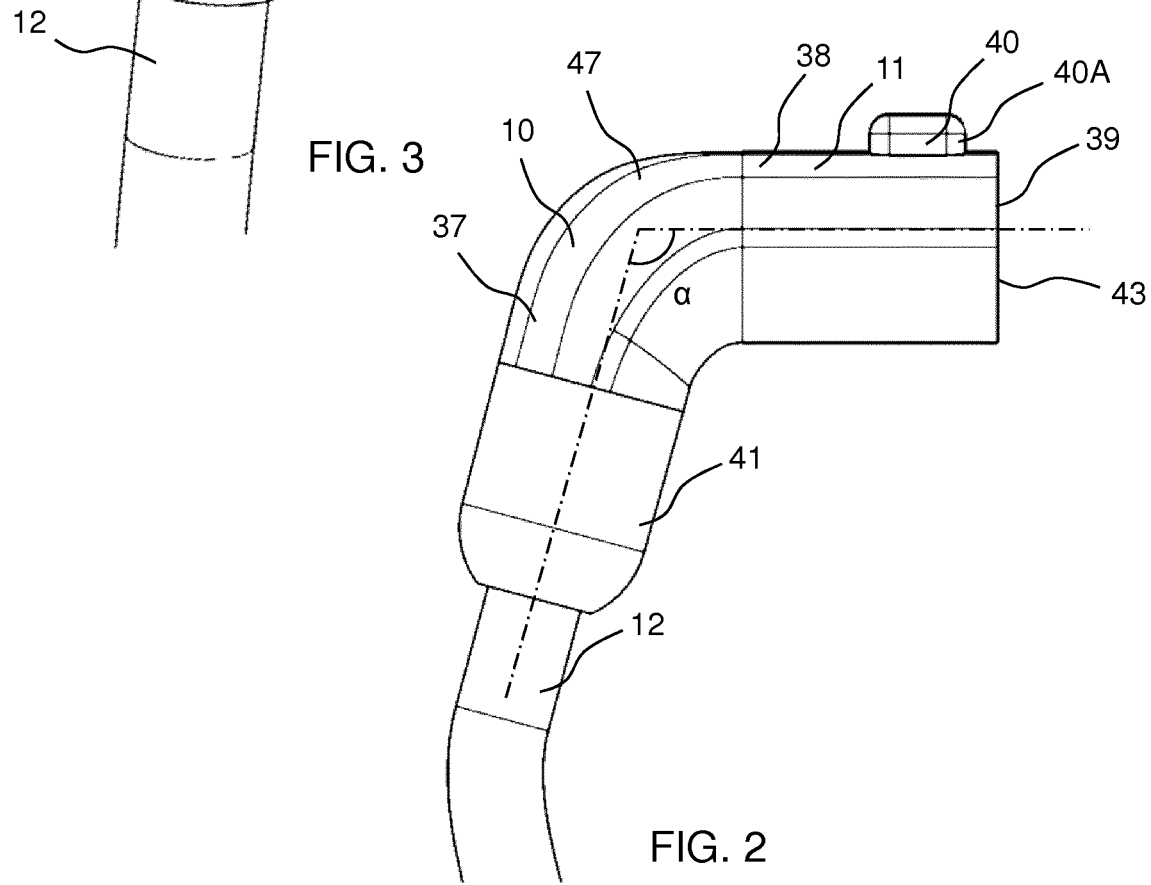
FIG. 3
FIG. 2

CONNECTOR ARRANGEMENT, A SYSTEM FOR EXTRACORPOREAL BLOOD TREATMENT AND A METHOD FOR PRIMING A FLUID CHAMBER OF A BLOOD TREATMENT UNIT

PRIORITY CLAIM

The present application is a National Phase of International Application No. PCT/EP2017/079850, filed Nov. 21, 2017, which claims priority to Swedish Application No. 1651563-7, filed Nov. 29, 2016, the entire contents of each of which are incorporated herein by reference and relied upon.

TECHNICAL FIELD

The present disclosure relates to the field of renal replacement therapy for extracorporeal blood treatment, and in particular to a connector arrangement, a system for extracorporeal blood treatment and a method for priming. The disclosure also relates to a computer program and a computer program product.

BACKGROUND

Renal replacement therapy is used for patients that have poorly functioning kidneys, and need to treat their blood outside their bodies. An extracorporeal blood treatment can be used to extract undesirable substances or molecules from the patient's blood, and, if necessary, to add desirable substances or molecules to the blood. The extracorporeal blood treatment is accomplished by passing blood through a blood treatment unit, e.g. a dialyzer or a hemofilter. A membrane separates the blood treatment unit into a blood chamber and a fluid chamber. Blood withdrawn from the patient is introduced into the blood chamber. The membrane is semipermeable to selectively allow matter in the blood to flow across the membrane from the blood chamber into the fluid chamber. The membrane also selectively allows matter in the fluid chamber to flow across the membrane into the blood chamber, depending on the type of treatment.

The membrane may be divided into a plurality of multiple hollow fibers in a hollow fiber structure to maximize the boundary area between the blood chamber and the fluid chamber. In the treatment unit, the blood may flow along the inside of the fibers and fluid along the outside of the fibers, or vice versa. The flows are normally counter current to increase the efficiency of the treatment. Conceptually the semipermeable membrane can be viewed as a perforated sheet.

Before the treatment unit can be used in a treatment, it has to be primed in order to remove any air inside the treatment unit. After the priming has been completed it is desired to maintain the fluid path and the blood path unbroken, and for example the connectors to the blood treatment unit shall not have to be moved to start a treatment. A commonly used procedure is to first prime the blood chamber from the bottom of the blood chamber to the top of the blood chamber with priming fluid that is introduced via a lower connection to the blood chamber. Any air in the blood chamber will then escape via an upper connection of the blood chamber. Thereafter the treatment unit is turned about 180 degrees such that the fluid chamber also can be primed from the bottom of the fluid chamber to the top of the fluid chamber with priming fluid via a connection to a now lower connection of the fluid chamber. Any trapped air will then escape from a now upper connection of the fluid chamber. This because the priming fluid is heavier than air and will fill the treatment unit via the lower connection from the bottom of the treatment unit and the air in the treatment unit will be pressed out of the treatment unit via the upper connection. This commonly used procedure is illustrated e.g. in U.S. Pat. No. 8,875,748B2 and EP0747074B1. By turning the treatment unit, the fluid chamber can be primed from its bottom to its top without having to change the position of the connectors to the treatment unit, and without passing priming fluid from a waste line to the fluid chamber. However, the commonly used procedure to turn the treatment unit during priming requires an operator to manually turn the treatment unit, either by means of a rotatable holder holding the treatment unit, or by removing the treatment unit from the holder, turn the treatment unit upside down, and put it back into the holder.

SUMMARY

The priming procedure of the treatment unit has to be taught to the operator, and it is advantageous that the procedure is easy. Further, the rotatable arm is exposed to wear and often becomes broken and has to be repaired. Thus, there is a need for an improved solution of priming the treatment unit.

It is an objective of the disclosure to alleviate at least some of the drawbacks with the prior art. It is a further objective to decrease the manual operation and to increase the degree of automatization of the priming procedure of the blood treatment unit. It is a further objective to reduce the time for setting up a blood treatment system and make it ready for treatment. It is a still further objective to reduce the overall costs for the blood treatment system.

These objectives and others are at least partly achieved by the arrangement, system and the method according to the independent claims, and by the embodiments according to the dependent claims.

According to a first aspect, the disclosure relates to a connector arrangement for connecting to a fluid chamber of a blood treatment unit for extracorporeal blood treatments. The connector arrangement includes a connector device with a connector body comprising a port opening and an interior wall defining a port space designed to receive a first fluid port of the fluid chamber. The connector device also incorporates a fluid path extending from the port space to a first end opening of the connector device and an air path extending from the port space to a second end opening of the connector device, wherein the fluid path and the air path are separate paths.

With the connector arrangement, the treatment unit does not have to be turned during priming of the same. The whole treatment unit can be primed while the treatment unit is in a fixed, same position. During priming, priming fluid is conducted via the fluid path into the fluid chamber, and at the same time, air trapped in the fluid chamber will find its way out from the fluid chamber via the air path in the connector device. The fluid path and the air path extend inside the connector body of the connector device.

According to some embodiments, the connector arrangement includes a guiding arrangement incorporating a fluid lumen and an air lumen, wherein the fluid lumen is connected to the fluid path at the first end opening, and the air lumen is connected to the air path at the second end opening. By means of the guiding arrangement, the connector device may be connected to a fluid line and a drain line of a renal replacement therapy machine.

According to some embodiments, the connector body defines a first body part connected to the guiding arrangement and a second body part incorporating the port opening and the port space.

According to some embodiments, the first body part and the second body part are arranged with an intermediate angle α of 70°-160°. Thereby the connector device may be easily held with one hand by an operator.

According to some embodiments, the connector arrangement includes a locking arrangement arranged to releasably lock the connector device to the first fluid port of the fluid chamber. Thereby the connector arrangement may be securely maintained in place to the first fluid port of the fluid chamber.

According to a second aspect, the disclosure relates to a system for extracorporeal blood treatment. The system includes a blood treatment unit having a blood chamber, a fluid chamber and a semipermeable membrane that separates the chambers from each other. The blood chamber is provided with a first blood port and a second blood port, and the fluid chamber is provided with a first fluid port and a second fluid port. The system further includes a fluid circuit including the fluid chamber, and a connector arrangement as described herein.

As the system includes the connector arrangement where the fluid chamber may be primed by passing priming fluid into the fluid chamber and air out of the fluid chamber via the same fluid port, the treatment unit does not have to be turned during priming of the same. The whole treatment unit can be primed while the treatment unit is in a fixed, same position.

The operation of the system may thus be simplified as there is no need for the operator to turn the treatment unit. Further, the automatization degree of the system can be increased, as all steps of a start-up sequence including the priming can be automatically performed without operator interaction. The time for starting up the system can thus be reduced.

As there is no need to turn the treatment unit, there is no need for a rotatable arm. The overall cost of the system may thus be reduced, as a rotatable arm is an expensive part of a machine of the system that now can be obviated.

According to some embodiments, the first fluid port is located above the second fluid port when the blood treatment unit is arranged in an operating position to a cabinet wall of a blood treatment machine of the system, and wherein the connector device is connected to the first fluid port. Thereby air trapped in the fluid chamber will be allowed to escape from the fluid chamber via the air path of the connector device.

According to some embodiments, the fluid circuit includes a drain line connected to the second fluid port for passing of waste fluid from the fluid chamber, wherein the air lumen is connected to the drain line for passing of air from the connector arrangement to the drain line. Thereby air from the fluid chamber can be conducted out of the system via the drain line.

According to some embodiments, the fluid circuit includes a fluid line connected to a fluid lumen, wherein the fluid lumen is connected to the fluid path at the first end opening. Thereby fluid such as priming fluid may be conducted to the fluid chamber from the fluid line. The fluid line may be an internal line of a renal replacement therapy machine of the system.

According to some embodiments, the system includes a fluid pump for pumping fluid in the fluid circuit, and a control unit configured to control the fluid pump to pump fluid into the fluid chamber whereby the fluid chamber is filled with fluid and air trapped in the fluid chamber is evacuated via the air path and the air lumen to the drain line.

According to some embodiments, the control unit is configured to monitor a filling criterion for the fluid chamber, and to stop the filling when the criterion has been fulfilled.

According to some embodiments, the filling criterion includes: a predetermined time limit for the time period for filling the fluid chamber, and/or a predetermined pressure limit on the pressure in any of the drain line or the connecting line and/or a predetermined fluid level limit in a fluid accumulator arranged to the drain line and/or a presence of air and/or presence of liquid in any of the drain line or the connecting line.

According to a third aspect, the disclosure relates to a method for priming a fluid chamber of a blood treatment unit of a system according to any of the embodiments as described herein, wherein the connector device is attached to the first fluid port. The method includes:
  preventing fluid from escaping the fluid chamber via the second fluid port;
  filling the fluid chamber with fluid passed via the fluid line, the fluid lumen and the fluid path, meanwhile air trapped in the fluid chamber escapes via the air path and the air lumen.

The fluid may be a liquid such as water or a water solution such as priming fluid or dialysis fluid.

According to some embodiments, the blood treatment unit is arranged in an operating position on a machine of the system such that the first fluid port is located above the second fluid port before the filling starts, whereby the filling includes filling the fluid chamber from the bottom of the fluid chamber and up. The fluid is thus passed via the first fluid port into the fluid chamber, but because of gravity the fluid is forced downwards in the fluid chamber and thereby fills the fluid chamber from the bottom and up. As no fluid is allowed to escape through the lowermost second fluid port, the fluid keeps filling the fluid chamber.

According to some embodiments, the method includes stopping the filling when a filling criterion has been fulfilled.

According to some embodiments, the system includes a blood line connected to the blood chamber and the priming of the fluid chamber is part of a priming procedure of the blood treatment unit including priming of the blood chamber.

According to some embodiments, the filling of the fluid chamber and priming of the blood chamber is performed when the blood treatment unit is kept in substantially the same orientation.

According to some embodiments, the method includes passing the escaped air to a drain line of the fluid circuit.

According to some embodiments, the method includes preventing the fluid from escaping the fluid chamber by closing a valve unit arranged to a drain line arranged to the second fluid port.

According to a fourth aspect, the disclosure relates to a computer program configured to operate on a system for extracorporeal blood treatment, wherein the computer program includes computer instructions, which computer program, when downloaded and executed by a processor of the control unit, causes the control unit to perform any of the method steps as disclosed herein.

According to a fifth aspect, the disclosure relates to a computer readable medium including computer instructions that, when executed by the processor of a control unit of a system for extracorporeal blood treatment, cause the control unit to perform the method according to any of the method steps as disclosed herein.

BRIEF DESCRIPTION OF THE DRAWINGS

FIG. 2 illustrates a connector arrangement according to some embodiments.

FIG. 3 illustrates the connector arrangement in FIG. 2 in an angled front view.

FIG. 4 is illustrating an example of a fluid port.

DETAILED DESCRIPTION

Figure 1:
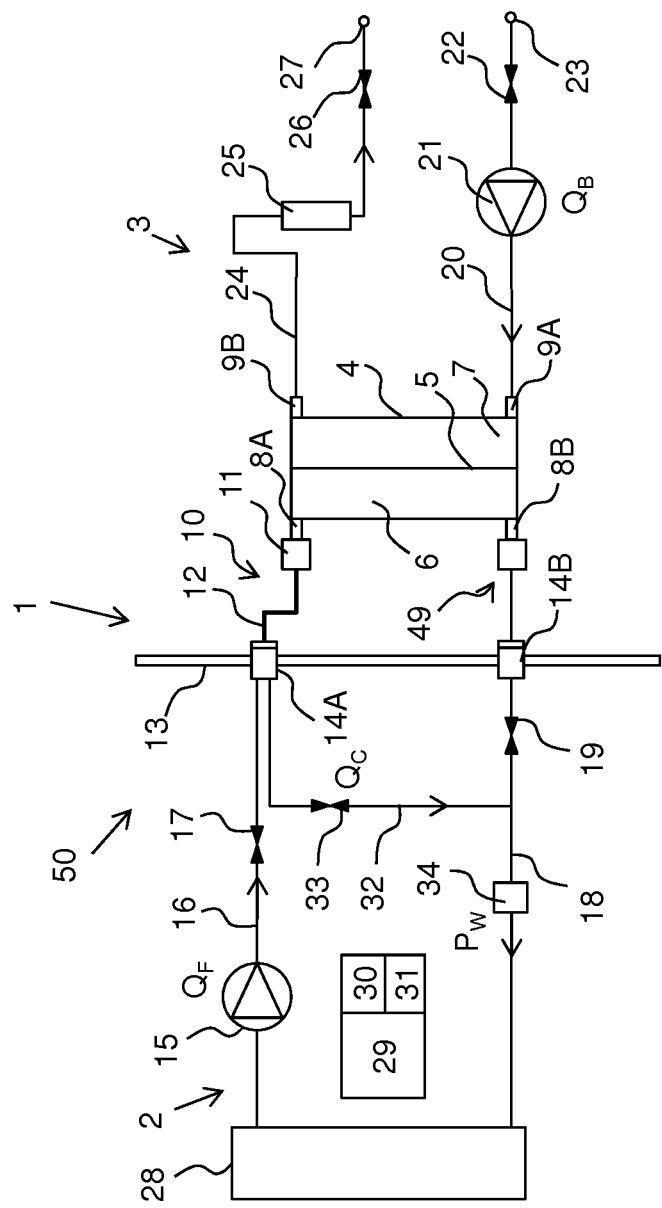
FIG. 1 illustrates a system for renal replacement therapy according to some embodiments.

In FIG. 1 a system 1 for renal replacement therapy is illustrated. The system 1 includes a renal replacement therapy machine 50, a dialysis fluid circuit 2 and an extracorporeal blood circuit 3 including a blood line and a blood treatment unit 4. The blood treatment unit 4 may be a filter unit or a dialyzer. The blood treatment unit 4 includes a semipermeable membrane 5 that separates a fluid chamber 6 and a blood chamber 7 of the blood treatment unit 4. The semipermeable membrane 5 may be divided into a multiple of hollow fibers in a hollow fiber structure. Conceptually the semipermeable membrane 5 may however be viewed as a sheet perforated by holes or pores.

The blood line includes an arterial line 20 and a venous line 24. The blood line is connected to the blood chamber 7 of the blood treatment unit 4. Thus, the arterial line 20 is connected to a first blood port 9A of the blood chamber 7 of the blood treatment unit 4 and the venous line 24 is connected to a second blood port 9B of the blood chamber 7 of the blood treatment unit 4. The arterial line 20 is fitted with a peristaltic pump 21 arranged to supply a blood flow $Q_B$ in the arterial line 20. The arterial line 20 is further fitted with an arterial valve unit 22 for closing or opening the arterial line 20 to a blood access point 23 of the arterial line 20. The blood access point 23 may be connected via a needle to a patient for withdrawal of blood. The blood access point 23 may instead be connected to a blood bag (not shown) for withdrawal of blood from the blood bag. The venous line 24 is fitted with a drip chamber 25.

The venous line 24 is further fitted with a venous valve unit 26 for closing or opening the venous line 24 to a blood access point 27 of the venous line 24.

The fluid circuit 2 includes a fluid line 16 and a drain line 18. The fluid line 16 is connected to a fluid unit 28 and to a first wall connector 14A or port arranged to a cabinet wall 13 of the renal replacement therapy machine 50, for transfer of fluid from the fluid unit 28 to the first wall connector 14A. A connector arrangement 10 is detachably connected to the first wall connector 14A or port with a corresponding connector, and to a first fluid port 8A of the fluid chamber 6 of the blood treatment unit 4, for further transfer of the fluid from the first wall connector 14A to the fluid chamber 6 via the first fluid port 8A. The connector arrangement 10 thus connects the fluid line 16 to the fluid chamber 6 of the blood treatment unit 4 when connected to the first fluid port 8A. The fluid circuit 2 further includes a drain line 18 arranged to be connected to a second wall connector 14B or port arranged to the cabinet wall 13, for transfer of used fluid from the second wall connector 14B to the fluid unit 28, e.g. to a drain. The fluid circuit 2 further includes another connector arrangement 49 detachably connected to a second fluid port 8B of the fluid chamber 6 of the blood treatment unit 4, and the second wall connector 14B with a corresponding connector, for transfer of used fluid from the fluid chamber 6 to the second wall connector 14B. The first fluid port 8A is here an inlet port to the fluid chamber 6, and the second fluid port 8B is an outlet port from the fluid chamber 6. The first wall connector 14A may include two separate passages or connectors for separate transfer of fluid and air.

The fluid line 16 is further fitted with a fluid pump 15 arranged to supply a fluid flow $Q_F$ in the fluid line 16 and the connector arrangement 10. During treatment, the fluid flows via the connector arrangement 10 into the fluid chamber 6 of the blood treatment unit 4 where the blood treatment takes place. Used fluid is passed out of the fluid chamber 6 through the second fluid port 8B, the another connector arrangement 49, the second wall connector 14B and the drain line 18 to the fluid unit 28. The used fluid may be passed e.g. to a drain (not shown). The fluid line 16 is further fitted with a fluid valve unit 17 for restricting the fluid flow in the fluid line 16. The drain line 18 is fitted with a drain valve unit 19 for restricting the used fluid flow in the drain line 18. The drain line 18 may further be fitted with a drain pump (not shown) arranged to supply a drain flow $Q_w$ in the drain line 18.

The connector arrangement 10 includes a connector device 11 arranged to be connected to the first fluid port 8A. The connector arrangement 10 further includes a guiding arrangement 12 arranged to be connected to the first wall connector 14A via a corresponding connector. The guiding arrangement 12 and the connector device 11 are fluidly interconnected. According to some embodiments, the system 1 further includes a connecting line 32 arranged to fluidly connect the guiding arrangement 12 to the drain line 18. The connecting line 32 is connected to the first wall connector 14A on the inside of the machine 50 at one end, and to the drain line 18 at the other end. The connecting line 32 is fitted with a connecting valve unit 33 for restricting a flow $Q_c$ in the connecting line 32. The drain line 18 is fitted with a detection device 34 for sensing a pressure $P_w$ in the drain line 18, or for sensing the presence of fluid, e.g. air or priming fluid.

The renal replacement therapy system 1 is further arranged with a control unit 29 for controlling the operations of the system 1, e.g. the fluid flow $Q_F$ induced by the fluid pump 15, the blood flow $Q_B$ induced by the blood pump 21; and restriction of the fluid valve unit 17, the used fluid valve unit 19, the arterial valve unit 22, the venous valve unit 26, the connecting valve unit 33, and for monitoring the detection device 34. The control unit 29 includes a processor 30 and a memory 31. The memory 31 includes a computer program configured to operate on the system 1. The computer program includes computer instructions, that when downloaded and executed by the processor 30, causes the control unit 29 to perform any of the steps of the method as will be described in the following. The control unit 29 is thus programmed to perform the method. The computer instructions may be stored on a computer readable medium, and loaded into the memory 31 of the control unit 29. The computer readable medium may be a non-transitory computer readable medium. The processor may be made up of one or several Central Processing Units (CPUs). The memory 31 may be made up of one or several memory units. The memory may be a non-transitory computer readable memory. The control unit 29 is connected to the different pumps and units by wire or by wireless connection, but any connections in the figures are here removed in order to make the drawing more legible.

In FIG. 2 a part of the connector arrangement 10 is illustrated in more detail. The connector device 11 includes a connector body 47 defined by a first body part 37 and a second body part 38. The first body part 37 is arranged to be connected to the guiding arrangement 12 at one end of the first body part 37, and the second body part 38 arranged to be connected to the first fluid port 8A (FIGS. 1, 4) at one end of the second body part 38. The first body part 37 is here fastened and connected to the guiding arrangement 12 by means of a fastening arrangement including an end collar 41, as illustrated in greater detail in FIG. 5. Further to FIG. 2, the second body part 38 is at the end thereof provided with a port opening 43 and a port space 39 designed for receiving the port 8A. The first body part 37 and the second body part 38 may be made in one piece, or alternatively in two or more pieces that are joined by a suitable joining method. The first body part 37 and the second body part 38 are angled in respect to each other, thus arranged with an intermediate angle α between 70°-160°, and more particular between 90°-120°, to give the connector device 11 a shape of a handle, that is, a pistol shape, and to create a smooth connection between the fluid chamber 6 and the guiding arrangement 12. The guiding arrangement 12 here includes a double lumen tube. According to another embodiment, the guiding arrangement 12 includes two separated tubes.

The connector device 11 is arranged with a locking arrangement 40 including a locking button 40A and a jaw part 40B (FIG. 3) in order to releasable lock the connector device 11 to the first fluid port 8A, as will be further described in the following.

In FIG. 3 the part of the connector arrangement 10 shown in FIG. 2 is illustrated from an angled front view such that the port opening 43 and the port space 39 are visible. Further inside the connector device 11, beyond the port space 39, a separating wall 42 is located. The port space 39 is located between the port opening 43 and the separating wall 42. The port space 39 is designed to receive the first fluid port 8A (FIG. 1), when the first fluid port 8A is inserted into the port opening 43. The connector device 11 comprises a circular interior wall 50 limiting or enclosing the port space 39. The interior wall 50 is constructed with a dimension such that the first fluid port 8A can be received into the port space 39 and achieve a fluid tight connection.

The locking button 40A is arranged to an upper side of the second body part 38 of the connector device 11. The jaw part 40B is arranged to the second body part 38 and mechanically linked to the locking button 40A. When no pressure is exerted on the locking button 40A, thus, the locking button 40A is released, the jaw part 40B protrudes inside the port space 39. When the locking button 40A is pressed down, e.g. by a thumb of a user, the jaw part 40B is pushed down and away from the port space 39. The user may lock the connector device 11 to the first fluid port 8A by pressing on the locking button 40A whereby the jaw part 40B is pushed away from, and out of, the port space 39; inserting the first fluid port 8A into the opening of the connector device 11 and then releasing the locking button 40A whereby the jaw part 40B protrudes into the port space 39 through the interior wall 50 and mate with a corresponding groove 60 on the fluid port 8A (FIG. 4). The jaw part 40B will then secure the connector device 11 to the first fluid port 8A. The port opening 43 and port space 39 fit snuggly with the first fluid port 8A when the first fluid port 8A is inserted into the port space 39 such that no air or fluid may escape between the connector device 11 and the first fluid port 8A. When the first fluid port 8A is correctly inserted into the port space 39 of the connector device 11 and the locking button 40A is released, a tooth or several teeth of the jaw part 40B fit with and are inserted into the groove 60 in the first fluid port 8A and lock the connector device 11 to the first fluid port 8A. When the locking button 40B is pressed down, the tooth or teeth are withdrawn from the groove 60 to release the first fluid port 8A.

In FIG. 4 an example of a fluid port is illustrated in isolation. The fluid port may be any of the first fluid port 8A and the second fluid port 8B. The fluid port is e.g. a Hansen port. The fluid port is arranged with a tube intended to be inserted into the port space 39. The tube is provided with an outer circumferential groove 60.

Figure 5:
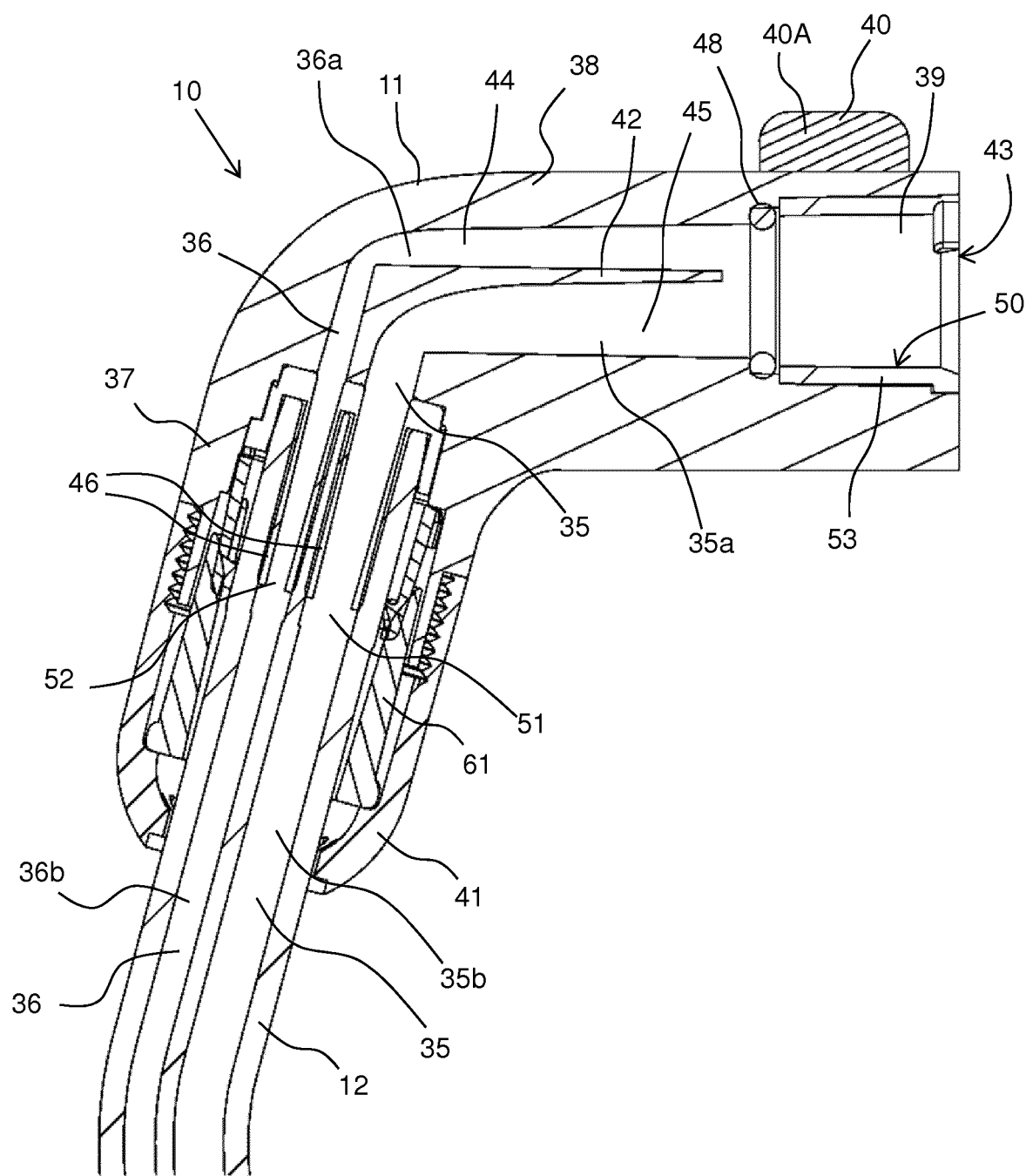
FIG. 5 is illustrating a cross-section of the connector arrangement in FIG. 2.

In FIG. 5 a cross section of the part of the connector arrangement 10 shown in FIG. 2 is illustrated. The first fluid port 8A is here not inserted into the port space 39. However, when the first fluid port 8A is received into the port space 39, the tube of the first fluid port 8A fits snuggly into the port space 39 such that a fluid tight coupling is achieved. The integrity of the coupling may be enhanced with a ring shaped seal tightening 48 between the connector device 11 and the tube of the first fluid port 8A. The ring shaped seal tightening 48 is arranged in a proximal part of the port space 39, in a groove in the interior wall 50 of the second body part 38 limiting the port space 39. When the first fluid port 8A is received into the port space 39, the distal end of the tube of the first fluid port lay against the ring shaped seal tightening 48. The connector device 11 may also include a socket or collet 53 fitted in the port space 39 and aligned with the interior wall 50, to accommodate the tube of the first fluid port 8A.

In some embodiments, the connector arrangement 10 defines an air channel 36 and a fluid channel 35 that will be explained in detail in the following with reference to the FIGS. 1-4. The air channel 36 is arranged for passing of air from the fluid chamber 6 (FIG. 1) via the first fluid port 8A. The fluid channel 35 is arranged for passing of fluid from the fluid line 16 (FIG. 1) to the fluid chamber 6 via the same first fluid port 8A. Further, the passing of air from the fluid chamber 6 via the first fluid port 8A and passing of fluid from the fluid line 16 to the fluid chamber 6 via the same first fluid port 8A may be made simultaneously. Also, the fluid channel 35 and the air channel 36 are separate channels. The air channel 35 extends from the port space 39 to the first wall connector 14A. The fluid channel 35 extends from the first wall connector 14A to the port space 39. The fluid channel 35 is thus arranged to be in fluid communication with the fluid line 16 and the first fluid port 8A, for passing of fluid from the fluid line 16 to the fluid chamber 6. Further, the air channel 36 is arranged to be in fluid communication with the first fluid port 8A and the first wall connector 14A, for transfer of fluid, e.g. air, from the fluid chamber 6 to the connecting line 32.

One part of the fluid channel 35 is formed by a fluid path 35a in the connector device 11, and another part of the fluid channel is formed by a fluid lumen 35b in the guiding arrangement 12. One part of the air channel 36 is formed by an air path 36a in the connector device 11, and another part of the air channel 36 is formed by an air lumen 36b in the guiding arrangement 12. The fluid path 35a extends from the (inner end of the) port space 39 to a first end opening 51 of the connector device 11. The fluid lumen 35b is connected to the fluid path 35a at the first end opening 51. The air path 36a extends from the (inner end of the) port space 39 to the second end opening 52 of the connector device 11. The air lumen 36b is connected to the air path 36a at the second end opening 52. The fluid path 35a and the air path 36a are separate paths. The fluid path 35a and the air path 36a are in one embodiment parallel paths. The fluid path 35a and the air path 36a may have circular cross sections. The cross section of the air path 36a is in embodiment smaller than the cross section of the fluid path 35a. For example, the cross section of the air path 36a may be less than half the cross section of the fluid path 35a. As illustrated in FIG. 5, the separating wall 42 separates a cavity inside of the first body part 37 of the connector device 11 into an upper compartment 44 constituting a part of the air path 36a and a lower compartment 45 constituting a part of the fluid path 35a. The air path 36a thus includes the upper compartment 44, and the fluid path 35a includes the lower compartment 45. In other words, the separating wall separates the air path 36a and the fluid path 35a. When the connector arrangement 10 is being used and attached to the first fluid port 8A, the connector device 11 should preferably be in a position such that the upper compartment 44 is located above the lower compartment 45.

As can be concluded from the above, the upper compartment 44 is part of the air channel 36, and the lower compartment 45 is part of the fluid channel 35. The connector device 11 thus at least partly incorporates the fluid channel 35, and at least partly incorporates the air channel 36. The fluid channel 35 and the air channel 36 debouch into the port space 39 in the second body part 38 inside the connector device 11 between an end of the separating wall 42 and the port opening 43. The upper compartment 44 and the lower compartment 45 may together form a cylinder formed space in the connector device 11. The separating wall 42 separates this cylinder formed space in the axial direction of the cylinder. The separating wall 42 may thus have a rectangular shape. The separating wall 42 separates the cylinder shaped space such that the upper compartment 44 has a cross-sectional area that is smaller than the cross-sectional area of the lower compartment 45. Alternatively, the upper compartment 44 and/or the lower compartment 45 have circular cross-sections. The axial length of the separating wall 42 is of such dimension such that when the first fluid port 8A is fully inserted into the port space 39, the first fluid port 8A will not be hindered to be inserted into the port space 39. According to some embodiments, the axial length of the separating wall 42 has such a size such that the fluid passed in the fluid channel 35 has a low or none turbulence when entering the port space 39.

The fluid channel 35 and the air channel 36 thus extend inside the second body part 38 and from the second body part 38 further inside the first body part 37 and further into and inside the guiding arrangement 12 connected to the first body part 37. The guiding arrangement 12 thus incorporates parts of the fluid channel 35 and the air channel 36. The first body part 37 is arranged with two pipes 46 forming extensions of the upper compartment 44 and the lower compartment 45 into the first body part 37, and forms the first end opening 51 and the second end opening 51 of the device 11, respectively. Thus, a first pipe of the pipes 46 forms an extension of the upper compartment 44 and a second pipe of the pipes 46 forms an extension of the lower compartment. The pipes 46 protrude into a hollowness of the first body part 37. The guiding arrangement 12, here a double lumen tube, is inserted into the hollowness of the first body part 37 from the opposite side and each of the channels or lumens 35b, 36b of the double lumen tube is fitted to a respective pipe 46. The guiding arrangement 12 is fastened to the pipes 46 with a fastening arrangement including a clamping connection 61 and a screw joint. The clamping connection 61 comprises e.g. a compression ring arranged around the double lumen tube and a collar that is slid over the compression ring. The clamping connection 61 is held in place by the end collar 41 that is fastened to the first body part 37 by a screw joint. For that purpose, the end collar 41 has a threaded distal inside that mates with a threaded distal outside of the first body part 37. The clamping connection 57 is thus arranged partly inside the first body part 37 and partly inside the end collar 41. The end collar 41 is thread on the double lumen tube. When the threaded distal inside of the end collar 41 is engaged with the threaded distal outside of the first body part 37, the end collar 41 press on the clamping connection 61 such that the double lumen tube is pressed against the protruding pipes 46 in order to securely hold the double lumen tube in place. Thereby the guiding arrangement 12 is securely fastened to the connector device 11. When the end collar 41 is engaged to the first body part 37 by the screw joint, the outside of the end collar 41 has a smooth transition to the outside of the first body part 37.

The guiding arrangement 12 thus includes two tubes, either encapsulated as one double lumen tube or as two separate tubes. In other words, the guiding arrangement 12 incorporates a fluid lumen 35b and an air lumen 36b. One of the tubes includes or encapsulates part of the air channel 36 and the other tube includes or encapsulates part of the fluid channel 35. The tube including part of the air channel 36 is at one end connected to the pipe 46 extending from the upper compartment 44 in the connector device 11, and at the other end to the first wall connector 14A and to the connecting line 32. The other tube including part of the fluid channel 35 is at one end connected to the pipe 46 extending from the lower compartment 45 in the connector device 11, and at the other end to the first wall connector 14A and further to the fluid line 16. The pipes 46 thus extend the upper compartment 44 and the lower compartment 45 into a respective of the tubes of the guiding arrangement 12. More in detail, the fluid lumen 35b is connected to the fluid path 35a at the first end opening 51, and the air lumen 36b is connected to the air path 36a at the second end opening 52.

As can be seen from FIG. 1, the guiding arrangement 12 is connected to the first wall connector 14A via a corresponding mating connector of the double lumen tube, and is in connection with the fluid line 16 and connecting line 32 inside the machine 50 via the same first wall connector 14A. The first wall connector 14A thus connects the fluid line 16 with the fluid channel 35, and continues the air channel 36 into the connecting line 32. The connector device 11 is during use of the system 1 continuously connected to the first fluid port 8A. When the system 1 is not in use, or when the blood treatment unit 4 is being exchanged, the connector device 11 can be disconnected from the first fluid port 8A and arranged on a rest port (not shown) on the cabinet wall 13.

The connecting arrangement 10 is to be used during normal operation of the system 1, but is also intended to be used when performing a priming procedure during which the blood treatment unit 4 is primed without having to turn the blood treatment unit 4. Thus, the first fluid port 8A is always located above the second fluid port 8B when the blood treatment unit 4 is arranged in an operating position to the cabinet wall 13 of the renal replacement therapy machine 50. The blood treatment unit 4 is in the operating position both during the priming procedure and during treatments. There is thus no need to have a rotatable arm holding the blood treatment unit 4 that can turn the blood treatment unit 4.

Figure 6:
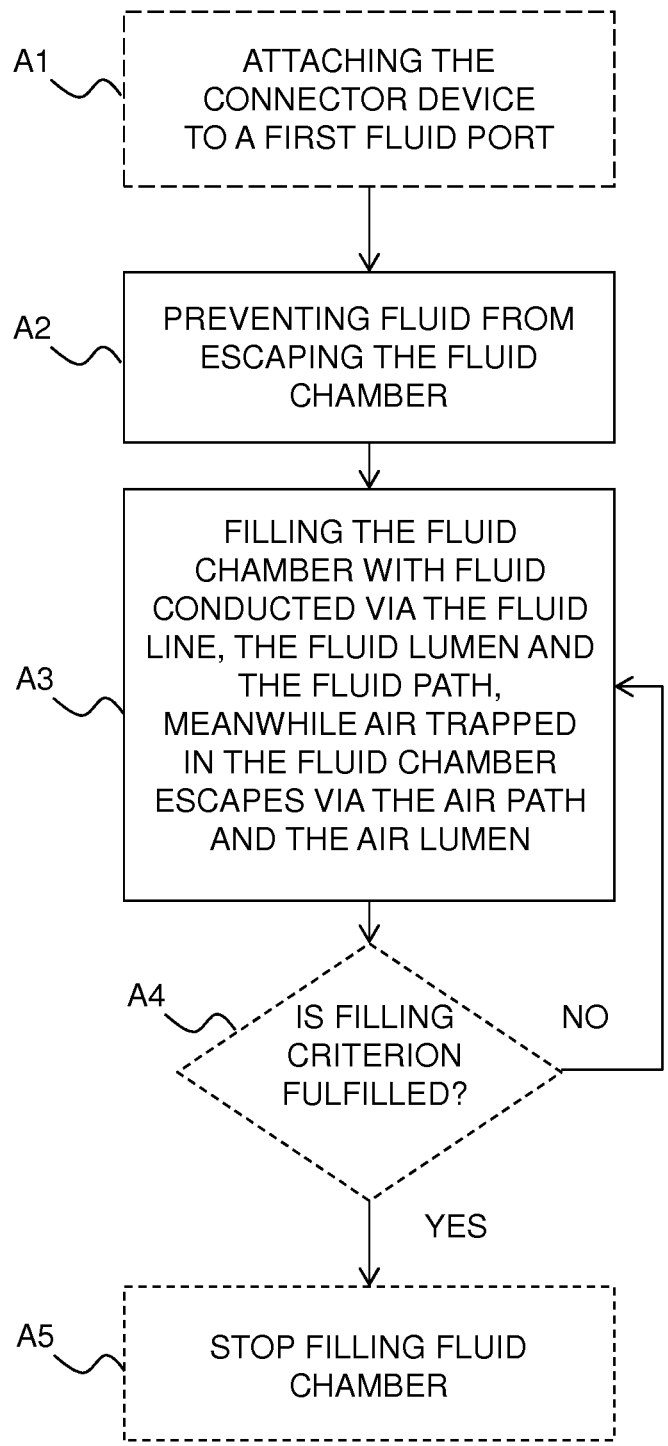
FIG. 6 is illustrating a flowchart of a method according to some embodiments.

Before the priming starts, the priming fluid is prepared while the system 1 is in bypass. The machine 50 is then dressed with a bloodline that is connected to the blood treatment unit 4. The bloodline and the blood treatment unit thus make up the blood circuit 3. The blood circuit 3 is then primed and the blood chamber 7 is thus filled with priming fluid. After the blood circuit 3 has been primed, the fluid circuit 2 is to be primed. The priming of the fluid circuit includes filling the fluid chamber 6 of the blood treatment unit 4 with a priming fluid. In FIG. 6 a flowchart of a method for priming the fluid chamber 6 is illustrated, and will hereinafter be explained with reference to this figure. The method may be initiated by attaching A1 the connector device 11 to the first fluid port 8A. This step is typically made by an operator of the system 1. When the connector device 11 is attached, the method includes to preventing A2 fluid from escaping the fluid chamber 6. This step can be performed by closing a drain valve unit 19 arranged to the drain line 18. The control unit 29 is configured to send a control signal to the drain valve unit 19 to close the drain valve unit 19. In a further step A3 the method includes filling the fluid chamber 6 with fluid passed via the fluid line 16 (FIG. 1), the fluid lumen 35b, the fluid path 35a (FIG. 5) and the first fluid port 8A into the fluid chamber 6, meanwhile air trapped in the fluid chamber 6 escapes via the air path 36a and the air lumen 36b via the same first fluid port 8A.

The control unit 29 is thus configured to send a control signal to the fluid pump 15 in order to control the pump 15 to pump priming fluid in the fluid circuit 2 and thus into the fluid chamber 6. As the priming fluid and any trapped air in the fluid chamber 6 are stopped from escaping the fluid chamber 6 via the second fluid port 8B more than e.g. filling the drain line 18 up to the drain valve unit 19, the fluid chamber 6 will be filled with priming fluid and air trapped in the fluid chamber 6 is evacuated via the air channel 36 to the drain line 18 via the connecting line 32. The control unit 29 is configured to send a control signal to the valve unit 33 in the connecting line to open the valve unit 33 such that air can be passed to the drain line 18. As an alternative, the connector arrangement 10 may include a vent (not shown) that is connected to the air line 36 in order to release air from the fluid chamber 6.

During treatment including priming etc., the blood treatment unit 4 is arranged in an operating position on a dialysis machine 50 such that the first fluid port 8A is located above the second fluid port 8B before the filling starts. The priming thus includes filling the fluid chamber 6 from the bottom of the fluid chamber 6 and up. Trapped air is passed via the air channel 36 as it is the only possible way for the air to escape from the fluid chamber 6. Priming fluid is passed via the fluid channel 35 into the fluid channel 35, so no air may escape via the fluid channel 35. The priming of the fluid chamber 6 and priming of the blood chamber 7 is performed when the blood treatment unit 4 is kept in substantially the same orientation.

The method may further include monitoring a filling criterion, see A4 in FIG. 6. If the filling criterion is fulfilled, the method includes in a step A5 to stop filling the fluid chamber 6. If the filling criterion has not been fulfilled, the method returns to step A3. The control unit 29 is thus configured to monitor the filling criterion for the fluid chamber 6, and to stop the filling when the criterion has been fulfilled. When the fluid chamber 6 has been filled with priming fluid, the priming fluid will start to be passed into the air channel 36 and further to the waste line 18. The filling criterion may include a predetermined time limit for the time period for filling the fluid chamber 6. The control unit 29 is then configured to monitor the time the fluid chamber 6 is being filled, and to stop the filling when the predetermined time limit has been reached. Alternatively the filling criterion includes a predetermined pressure limit on the pressure in any of the drain line 18 or the connecting line 32. The pressure $P_w$ in the drain line 18 and the connecting line 32 may be detected with the detector device 34 arranged to the drain line 18. The control unit 29 is then configured to monitor the pressure and to stop the filling when the pressure is equal to or has exceeded the predetermined pressure limit. The predetermined pressure limit is determined such that when such a pressure has been reached, there is no more air in the connecting line 32 and/or the drain line 18, and priming fluid has started to flow into the connecting line 32, and also, or within some time, in the drain line 18. In another alternative, the filling criterion includes a predetermined fluid level limit in a fluid accumulator (not shown) arranged to the drain line 18. The control unit 29 is then configured to monitor the fluid level in the fluid accumulator, and to stop the priming when the fluid level has reached or exceeded the predetermined fluid level limit.

Generally, the filling criterion shall take into account that there shall be no more air in the fluid chamber 6. Further, the filling criterion may include a presence of air and/or presence of liquid in any of the drain line 18 or the connecting line 32. The control unit 29 is then configured to monitors if there is any presence of air and/or presence of liquid in any of the drain line 18 or the connecting line 32.

The filling procedure of the fluid chamber 6 is stopped by opening the drain valve unit 19, and closing the connecting line valve unit 33. The priming fluid will continue to be passed into the fluid chamber 6 via the first fluid port 8A. The priming fluid will however now be passed out from the fluid chamber 6 via the second fluid port 8B that is located below the first fluid port 8A. The priming fluid will be passed via the drain line 18 to the fluid unit 28, e.g. to a drain. The system 1 may after the priming of the fluid circuit 2 be set into a recirculation mode, where the priming fluid is recirculated in the fluid circuit 2. The system 1 is now ready to start a treatment. It should be noted that the connector device 11 is attached to the blood treatment unit 4 during dressing the machine 50, and will then remain in the same attached position to the blood treatment unit 4 during priming and subsequent treatments.

While the invention has been described in connection with what is presently considered to be the most practical and preferred embodiment, it is to be understood that the invention is not to be limited to the disclosed embodiments, but on the contrary, is intended to cover various modifications and equivalent arrangements included within the scope of the appended claims.

The invention claimed is:

1. A connector arrangement configured to connect to a fluid chamber of a blood treatment unit for extracorporeal blood treatments, the blood treatment unit including a blood chamber, a fluid chamber, and a semipermeable membrane that separates the blood chamber and the fluid chamber, wherein the blood chamber is provided with a first blood port and a second blood port, and the fluid chamber is provided with a first fluid port and a second fluid port, the connector arrangement comprising:
   a connector device having a connector body comprising
      (i) a port opening located at an exterior of the connector device and (ii) an interior wall defining a port space configured to receive the first fluid port of the fluid chamber through the port opening, wherein the connector device further includes a fluid path extending from the port space to a first end opening of the connector device, and an air path extending from the port space to a second end opening of the connector device, and wherein the fluid path and the air path are separate paths.

2. The connector arrangement according to claim 1, which includes a guiding arrangement comprising a fluid lumen and an air lumen, wherein the fluid lumen is connected to the fluid path at the first end opening, and the air lumen is connected to the air path at the second end opening.

3. The connector arrangement according to claim 2, wherein the connector body defines a first body part connected to the guiding arrangement and a second body part incorporating the port opening and a port space.

4. The connector arrangement according to claim 3, wherein the first body part and the second body part are arranged with an intermediate angle of 70° to 160°.

5. The connector arrangement according to claim 1, which includes a locking arrangement positioned and arranged such that the connector device is releasably lockable to the first fluid port of the fluid chamber via the locking arrangement.

6. A system for extracorporeal blood treatment, including a blood treatment unit having the blood chamber, the fluid chamber and the semipermeable membrane that separates the blood chamber and the fluid chamber, wherein the blood chamber is provided with the first blood port and the second blood port, and the fluid chamber is provided with the first fluid port and the second fluid port, and wherein the system further includes a fluid circuit including the fluid chamber and the connector arrangement connected to the fluid chamber according to claim 1.

7. The system according to claim 6, wherein the first fluid port is located above the second fluid port when the blood treatment unit is arranged in an operating position to a cabinet wall of a blood treatment machine included in the system, and wherein the connector device is connected to the first fluid port.

8. The system according to claim 7, wherein the fluid circuit includes a drain line connected to the second fluid port for passing of waste fluid from the fluid chamber, wherein the air lumen is connected to the drain line for passing of air from the connector arrangement to the drain line.

9. The system according to claim 6, wherein the fluid circuit includes a fluid line connected to a fluid lumen, wherein the fluid lumen is connected to the fluid path at the first end opening.

10. The system according to claim 9, which includes a fluid pump for pumping fluid in the fluid circuit, and a control unit configured to control the fluid pump to pump fluid into the fluid chamber, whereby the fluid chamber is filled with fluid and air trapped in the fluid chamber is evacuated via the air path and the air lumen to the drain line.

11. The system according to claim 10, wherein the control unit is configured to monitor a filling criterion for the fluid chamber, and to stop the filling when the criterion has been fulfilled.

12. The system according to claim 11, wherein the filling criterion includes one of more criteria selected from the group consisting of: a predetermined time limit for the time period for filling the fluid chamber, a predetermined pressure limit on the pressure in any of the drain line or the connecting line, a predetermined fluid level limit in a fluid accumulator arranged to the drain line, and/or a presence of air and/or presence of liquid in any of the drain line or the connecting line.

13. A method for priming the fluid chamber of the blood treatment unit of the system according to claim 6, wherein the connector device is attached to the first fluid port, and wherein the method comprises:

preventing fluid from escaping the fluid chamber via the second fluid port; and filling the fluid chamber with fluid passed via the fluid line, the fluid lumen and the fluid path, while air trapped in the fluid chamber escapes via the air path and the air lumen.

14. The method according to claim 13, wherein the blood treatment unit is arranged in an operating position on a machine of the system such that the first fluid port is located above the second fluid port before the filling starts, whereby the filling includes filling the fluid chamber from the bottom of the fluid chamber and up.

15. The method according to claim 13, further comprising stopping filling of the fluid chamber when a filling criterion has been fulfilled.

16. The method according to any of the claims 13, wherein the system includes a blood line connected to the blood chamber and wherein the filling of the fluid chamber is part of a priming procedure of the blood treatment unit, the priming procedure including priming of the blood chamber.

17. The method according to claim 16, wherein the filling of the fluid chamber and the priming of the blood chamber are performed when the blood treatment unit is maintained in substantially the same orientation.

18. The method according to claim 13, further comprising passing the escaped air to a drain line of the fluid circuit.

19. The method according to claim 13, further comprising preventing the fluid from escaping the fluid chamber by closing a valve unit arranged to a drain line arranged to the second fluid port.

20. A connector arrangement for connecting to a fluid chamber of a blood treatment unit for extracorporeal blood treatments, the blood treatment unit including a blood chamber, a fluid chamber, and a semipermeable membrane that separates the blood chamber and the fluid chamber, wherein the blood chamber is provided with a first blood port and a second blood port, and the fluid chamber is provided with a first fluid port and a second fluid port, the connector arrangement comprising:

a connector device having a connector body comprising a port opening and an interior wall defining a port space configured to receive the first fluid port of the fluid chamber, wherein the connector device further includes a fluid path extending from the port space to a first end opening of the connector device, and an air path extending from the port space to a second end opening of the connector device, wherein the fluid path and the air path are separate paths; and a guiding arrangement that includes a fluid lumen and an air lumen, wherein the fluid lumen is connected to the fluid path at the first end opening, and the air lumen is connected to the air path at the second end opening.

21. A connector arrangement for connecting to a fluid chamber of a blood treatment unit for extracorporeal blood treatments, the blood treatment unit including a blood chamber, a fluid chamber, and a semipermeable membrane that separates the blood chamber and the fluid chamber, wherein the blood chamber is provided with a first blood port and a second blood port, and the fluid chamber is provided with a first fluid port and a second fluid port, the connector arrangement comprising:
- a connector device having a connector body comprising a port opening and an interior wall defining a port space configured to receive the first fluid port of the fluid chamber, wherein the connector device further includes a fluid path extending from the port space to a first end opening of the connector device, and an air path extending from the port space to a second end opening of the connector device, wherein the fluid path and the air path are separate paths; and
- a locking arrangement positioned and arranged lock such that the connector device is releasably lockable to the first fluid port of the fluid chamber via the locking arrangement.

* * * * *